United States Patent
Bhattacharyya et al.

(10) Patent No.: US 11,307,268 B2
(45) Date of Patent: Apr. 19, 2022

(54) COVALENTLY-BOUND ANTI-RELAXATION SURFACE COATINGS AND APPLICATION IN MAGNETOMETERS

(71) Applicant: HI LLC, Los Angeles, CA (US)

(72) Inventors: Sukanta Bhattacharyya, Belmont, CA (US); Daniel Sobek, Portola Valley, CA (US)

(73) Assignee: HI LLC, Los Angeles, CA (US)

( * ) Notice: Subject to any disclaimer, the term of this patent is extended or adjusted under 35 U.S.C. 154(b) by 414 days.

(21) Appl. No.: 16/679,048

(22) Filed: Nov. 8, 2019

(65) Prior Publication Data

US 2020/0191883 A1    Jun. 18, 2020

Related U.S. Application Data

(60) Provisional application No. 62/781,418, filed on Dec. 18, 2018.

(51) Int. Cl.
  *G01R 33/028* (2006.01)
  *C09D 201/10* (2006.01)
  *C09D 201/04* (2006.01)
  *G01R 33/26* (2006.01)

(52) U.S. Cl.
  CPC ......... *G01R 33/028* (2013.01); *C09D 201/04* (2013.01); *C09D 201/10* (2013.01); *G01R 33/26* (2013.01)

(58) Field of Classification Search
  USPC .......................................................... 324/304
  See application file for complete search history.

(56) References Cited

U.S. PATENT DOCUMENTS

| | | |
|---|---|---|
| 4,951,674 A | 8/1990 | Zanakis et al. |
| 5,189,368 A | 2/1993 | Chase |
| 5,192,921 A | 3/1993 | Chantry et al. |
| 5,254,947 A | 10/1993 | Chaillout et al. |

(Continued)

FOREIGN PATENT DOCUMENTS

| | | |
|---|---|---|
| CN | 104730484 | 6/2015 |
| CN | 107562188 | 1/2018 |

(Continued)

OTHER PUBLICATIONS

S. Knappe, V. Shah, P. Schwindt, L. Hoilberg, J. Kitching, L. Liew, and J. Moreland. A microfabricated atomic clock. Applied Physics Letters, 85(9):1460-1462, 2004.

(Continued)

*Primary Examiner* — Rodney E Fuller
(74) *Attorney, Agent, or Firm* — Branch Partners PLLC; Bruce E. Black

(57) ABSTRACT

A magnetometer includes a vapor cell having at least one wall, a chamber defined by the at least one wall, and alkali metal atoms disposed in the chamber to produce an alkali metal vapor in the chamber, wherein the at least one wall includes an oxide-containing interior surface; and an anti-relaxation coating disposed on the oxide-containing interior surface of the at least one wall of the vapor cell, wherein the anti-relaxation coating is a reaction product of the oxide-containing interior surface of the at least one wall with at least one mono- or dichlorosilane compound.

20 Claims, 3 Drawing Sheets

(56) References Cited

U.S. PATENT DOCUMENTS

| | | |
|---|---|---|
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Berwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 5/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 10,024,929 B2 | 7/2018 | Parsa et al. |
| 10,088,535 B1 | 10/2018 | Shah |
| 10,162,016 B2 | 12/2018 | Gabrys et al. |
| 11,131,729 B2 * | 9/2021 | Pratt ................ G01R 33/26 |
| 2004/0232912 A1 | 11/2004 | Tsukamoto et al. |
| 2005/0007118 A1 | 1/2005 | Kitching et al. |
| 2005/0046851 A1 | 3/2005 | Riley et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0199138 A1 | 7/2017 | Parsa et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2018/0003777 A1 | 1/2018 | Sorensen et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2019/0391213 A1 | 12/2019 | Alford |
| 2020/0025844 A1 | 1/2020 | Alford et al. |
| 2020/0056263 A1 | 2/2020 | Bhattacharyya et al. |
| 2020/0057115 A1 | 2/2020 | Jimenez-Martinez et al. |
| 2020/0057116 A1 | 2/2020 | Zorzos et al. |
| 2020/0072916 A1 | 3/2020 | Alford et al. |
| 2021/0114926 A1 * | 4/2021 | Ramirez-Serrano ................ G01R 29/0864 |
| 2022/0019011 A1 * | 1/2022 | Valev ................ G04F 5/14 |

FOREIGN PATENT DOCUMENTS

| | | |
|---|---|---|
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 12005/081794 | 9/2005 |
| WO | 2014/031985 | 2/2014 |
| WO | 2017/095998 | 6/2017 |

OTHER PUBLICATIONS

L. Nieradko, C. Gorecki, A. Douahi, V. Giordano, J.-C. Beugnot, J. Dziuban, and M. Moraja. New approach of fabrication and dispensing of micromachined cesium vapor cell. Journal of Micro/Nanolithography, MEMS, and MOEMS, 7(3):033013, 2008.

V. Maurice, J. Rutkowski, E. Kroemer, S. Bargiel, N. Passilly, R. Boudot, C. Gorecki, L. Mauri, and M. Moraja. Microfabricated vapor cells filled with a cesium dispensing paste for miniature atomic clocks. Applied Physics Letters, 1110(16):164103, 2017.

V. Maurice, J. Rutkowski, E. Kroemer, S. Bargiel, N. Passilly, R. Boudot, R. Chutani, S. Galliou, and C. Gorecki. Microfabricated vapor ceils for miniature atomic clocks based on post-sealing activated cesium dispensers. In International Frequency Control Symposium (IFCS), Joint with the 31st European Frequency and Time Forum (EFTF), pp. 636-637, Besançon, France, 2017.

F. Gong, Y. Jau, K. Jensen, and W. Happer. Electrolytic fabrication of atomic clock cells. Review of Scientific Instruments, 77(7):711-714, 2006.

M. Bick, H. Prinz, and A. Steinmetz. Ullmann's Encyclopedia of Industrial Chemistry, chapter Cesium and Cesium Compounds. Wiley Online Library, 2000.

(56) References Cited

OTHER PUBLICATIONS

L. Liew, S. Knappe, J. Moreland, H. Robinson, L. Hollberg, and J. Kitching. Microfabricated alkali atom vapor cells. Applied Physics Letters, 84(14):2694-2696, 2004.

L. Liew, J. Moreland, and V. Gerginov. Wafer-level filling of microfabricated atomic vapor cells based on thin-film deposition and photolysis of cesium azide. Applied Physics Letters, 90(11):114106, 2007.

S. Woetzel, V. Schultze, R. IJsselsteijn, T. Schulz, S. Anders, R. Stolz, and H. Meyer. Microfabricated atomic vapor cell arrays for magnetic field measurements. Review of Scientific Instruments, 82(3):033111,2011.

W. Wei, J. Shang, W. Kuai, S. Qin, T. Wang, and J. Chen. Fabrication of wafer-level spherical Rb vapor cells for miniaturized atomic clocks by a chemical foaming process. In 13th International Conference on Electronic Packaging Technology & High Density Packaging (ICEPTHDP), pp. 1639-1641, Guilin, Guangxi, China, 2012.

Larry J. Ryan, Robert E. Slocum, and Robert B. Steves; Miniature Vector Laser Magnetometer Measurements of Earth's Field; Polatomic, Inc.; May 10, 2004; 4 pages.

S. Theppakuttai, D. Shao, and S. Chen. Localized Laser Transmission Bonding for Microsystem Fabrication and Packaging. Journal of Manufacturing Processes, 6(1):24-31, 2004.

Evangelina Pensa, Emiliano Cortés, Gastón Corthey, Pilar Carro, Carolina Vericat, Mariano H. Fonticelli, Guillermo Benítez, Aldo A. Rubert, and Roberto C. Salvarezza; The Chemistry of the Sulfur-Gold Interface: In Search of a Unified Model; Accounts of Chemical Research 2012 45 (8), 1183-1192.

Helmut Hinterwirth, Stefanie Kappel, Thomas Waitz, Thomas Prohaska, Wolfgang Lindner, and Michael Lämmerhofer; Quantifying Thiol Ligand Density of Self-Assembled Monolayers on Gold Nanoparticles by Inductively Coupled Plasma—Mass Spectrometry; ACS Nano 2013 7 (2), 1129-1136.

Sasan Asiaei, Patricia Nieva and Mathilakath M. Vijayan; Fast Kinetics of Thiolic Self-Assembled Monolayer Adsorption on Gold: Modeling and Confirmation by Protein Binding; The Journal of Physical Chemistry B 2014 118 (47), 13697-13703.

Dong Yan, Jeremy A. Saunders, and, and G. Kane Jennings; Kinetics of Formation for n-Alkanethiolate Self-Assembled Monolayers onto Gold in Aqueous Micellar Solutions of C12E6 and C12E7; Langmuir 2002 18 (26), 10202-10212.

Syvain Karlen—Doctorate Thesis—"Fabrication and characterization of MEMS alkali vapor cells used in chip-scale atomic clocks and other atomic devices"—University of Neuchatel—Dec. 2017. (Relevant pages: Chapter 3 44-48).

A. Pelton. The Ca-Rb (Calcium-Rubidium) system. Bulletin of Alloy Phase Diagrams, 6(1):37, 1985.

Abstract for C.-H Lee, H. Guo, S. Radhakrishnam, A. Lal, C. Szekely, T. McClellan, and A. Pisano. A batch fabricated rubidium-vapor resonance cell for chip-scale atomic clocks. In Solid-State Sensors, Actuators and Microsystems Workshop, Hilton Head Island, SC, United States, 2005. (Abstract only found at https://www.jstage.jst.go.jp/article/ieejsmas/131/7/131_7_251/_article/-char/ja/).

Sahoo, H. K., Ottaviano, L., Zheng, Y., Hansen, O., & Yvind, K. (2018). Low temperature bonding of heterogeneous materials using Al2O3 as an intermediate layer. In Proceedings of SPIE (vol. 10535). [105350V] SPIE—International Society for Optical Engineering. (Proceedings of S P I E—International Society for Optical Engineering). DOI: 10.1117/12.2289526.

Douglas, R., van Veggel, A. A., Cunningham, L., Haughian, K., Hough, J., & Rowan, S. (2014). Cryogenic and room temperature strength of sapphire jointed by hydroxide-catalysis bonding. Class. Quantum Grav. 31 (2014) DOI: 10.1088/0264-9381/31/4/045001.

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Sarno Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

(56) References Cited

OTHER PUBLICATIONS

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics, Physical review letters. 109. 263903. 10.1103/PhysRevLett.109.263903.

Orang Alem, Rahul Mhaskar, Ricardo Jiménez-Martínez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roe, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0345-9601(69)90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE-NPSS. pp. 417-418.

Larry J. Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis atomic magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al; "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.

S. J. Seltzer, D. J. Michalak, M. H. Donaldson, M. V. Balabas3, S. K. Barber4, S. L. Bernasek5, M.-A. Bouchiat, A. Hexemer, A. M. Hibberd, D. F. Jackson Kimball, C. Jaye, T. Karaulanov, F. A. Narducci, S. A. Rangwala, H. G. Robinson, A. K. Shmakov, D. L. Voronov, V. V. Yashchuk, A. Pines, and D. Budker, "Investigation of antirelaxation coatings for alkali-metal vapor cells using surface science techniques," J. Chem. Phys. 133, 144703 (2010); https://doi.org/10.1063/1.3489922.

\* cited by examiner

COVALENTLY-BOUND ANTI-RELAXATION SURFACE COATINGS AND APPLICATION IN MAGNETOMETERS

CROSS-REFERENCE TO RELATED APPLICATIONS

This application claims the benefit of U.S. Provisional Patent Application Ser. No. 62/781,418, filed Dec. 18, 2018, which is incorporated herein by reference in its entirety.

FIELD

The present disclosure is directed to the area of covalently-bound anti-relaxation surface coatings. The present disclosure is also directed to methods, devices, and systems, such as magnetometers and magnetoencephalography systems and methods, that utilize these coatings.

BACKGROUND

In the nervous system, neurons propagate signals via action potentials. These are brief electric currents which flow down the length of a neuron causing chemical transmitters to be released at a synapse. The time-varying electrical current within an ensemble of neurons generates a magnetic field. Magnetoencephalography (MEG), the measurement of magnetic fields generated by the brain, is one method for observing these neural signals.

Existing technology for measuring MEG typically utilizes superconducting quantum interference devices (SQUIDs) or collections of discrete optically pumped magnetometers (OPMs). For MEG and other applications, the array of OPMS may have a large number of OPM sensors that are tightly packed. Such dense arrays can produce a high-resolution spatial mapping of the magnetic field, and at a very high sensitivity level. Such OPMs sensors can also be used for a wide range of other applications.

BRIEF SUMMARY

One embodiment is a magnetometer that includes a vapor cell having at least one wall, a chamber defined by the at least one wall, and alkali metal atoms disposed in the chamber to produce an alkali metal vapor in the chamber, wherein the at least one wall includes an oxide-containing interior surface; and an anti-relaxation coating disposed on the oxide-containing interior surface of the at least one wall of the vapor cell, wherein the anti-relaxation coating is a reaction product of the oxide-containing interior surface of the at least one wall with at least one mono- or dichlorosilane compound selected from:

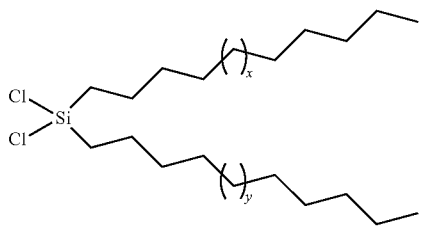

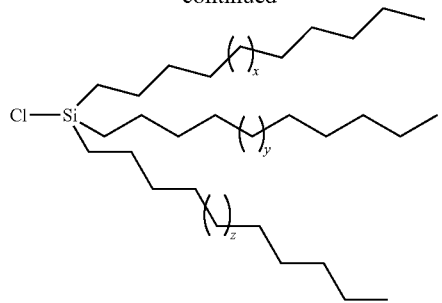

wherein x, y, and z, when present, are each independently an integer in a range of 0 to 40.

In at least some embodiments, the at least one mono- or dichlorosilane compound includes

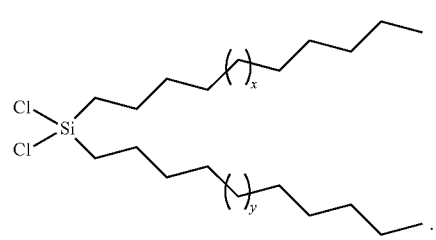

In at least some embodiments, the at least one mono- or dichlorosilane compound includes

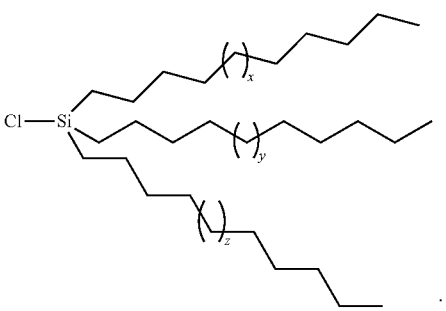

In at least some embodiments, x, y, and z, when present, are each independently an integer in a range of 5 to 25. In at least some embodiments, x, y, and z, when present, are equal.

In at least some embodiments, the oxide-containing interior surface includes silicon dioxide. In at least some embodiments, the oxide-containing interior surface includes aluminum oxide. In at least some embodiments, the vapor cell includes quartz. In at least some embodiments, the vapor cell includes sapphire. In at least some embodiments, the vapor cell includes glass.

Another embodiment is a magnetic field measurement system that includes at least one of any of the magnetometers described above; at least one light source configured for directing light to the at least one magnetometer; and at least one detector configured to receive light that passes through the at least one magnetometer.

In at least some embodiments, the magnetic field measurement system further includes at least one magnetic field generator configured to produce a magnetic field at the vapor cell of the magnetometer. In at least some embodiments, the magnetic field measurement system further includes a computing device coupled to the at least one detector.

Yet another embodiment is a method of making any of the magnetometers described above. The method includes contacting the oxide-containing interior surface of the at least one wall of the vapor cell with the at least one mono- or dichlorosilane compound; and reacting the mono- or diclorosilane compound with the oxide-containing interior surface to form an anti-relaxation coating on the oxide-containing interior surface.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
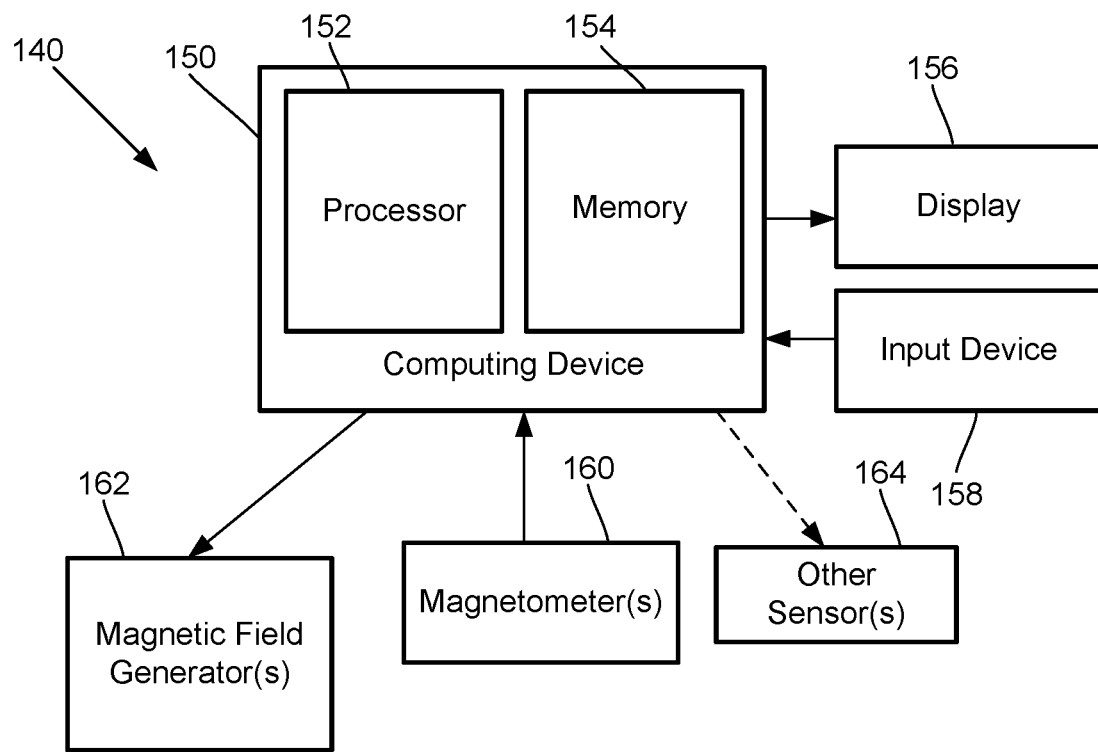
FIG. 1A is a schematic block diagram of one embodiment of a magnetic field measurement system, according to the invention.

The present disclosure is directed to the area of covalently-bound anti-relaxation surface coatings. The present disclosure is also directed to methods, devices, and systems, such as magnetometers and magnetoencephalography systems and methods, that utilize these coatings.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

The methods and systems are described herein using optically pumped magnetometers (OPMs). While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems, such as a biological signal detection system, described herein can be used to measure or observe electromagnetic signals generated by one or more magnetic field sources (for example, biological sources) of interest. The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be portable and used outside a magnetically shielded room.

A magnetic field measurement system, such as a biological signal detection system, can utilize one or more magnetic field sensors. Magnetometers will be used herein as an example of magnetic field sensors, but other magnetic field sensors may also be used in addition to, or as an alternative to, the magnetometers. FIG. 1A is a block diagram of components of one embodiment of a magnetic field measurement system 140 (such as a biological signal detection system.) The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode.

Figure 1B:
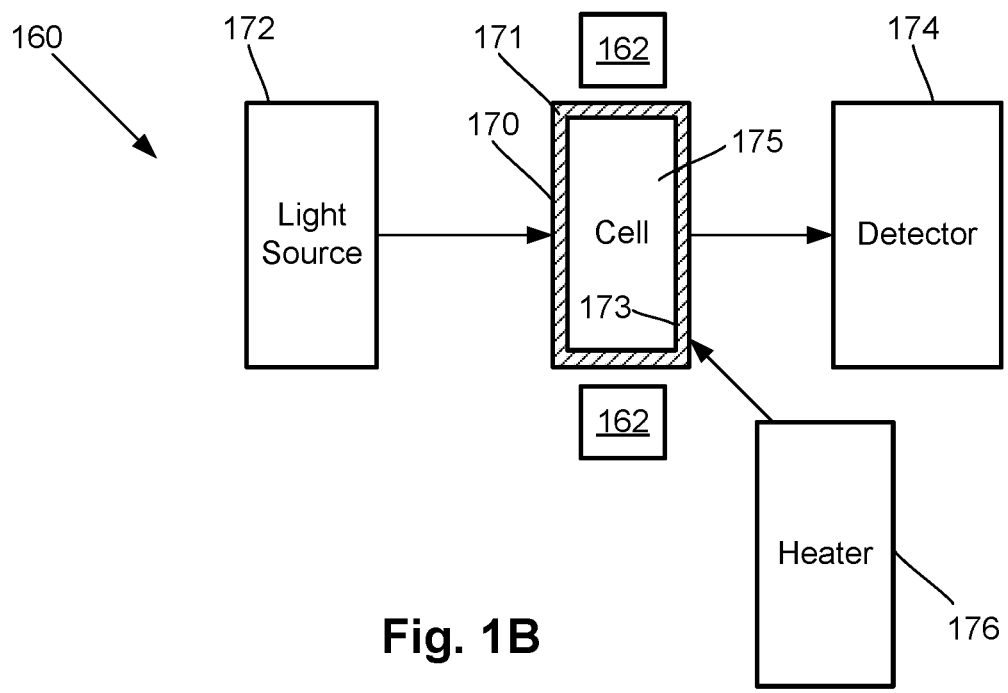
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell") such as an alkali metal vapor cell; a heating device 176 to heat the cell 170; a light source 172; and a detector 174. In addition, coils of a magnetic field generator 162 can be positioned around the vapor cell 170. The vapor cell 170 typically includes a chamber 175 surrounded by one or more walls 171. Interior surfaces 173 of the walls 171 form the boundary for the chamber 175. The vapor cell 170 can be made of any suitable material including, but not limited to, glass, quartz, sapphire, or the like which can include materials such as silicon dioxide or aluminum oxide. In the chamber 175, the vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and probe the gas cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
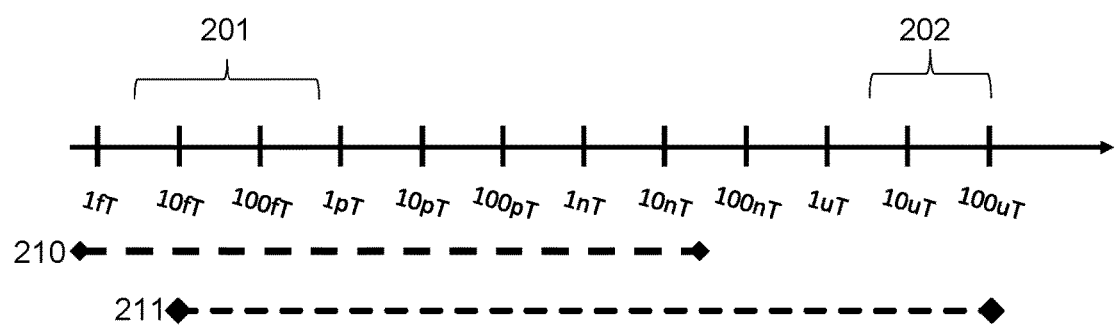
FIG. 2 shows a magnetic spectrum with lines indicating dynamic ranges of magnetometers operating in different modes.

FIG. 2 shows the magnetic spectrum from 1 fT to 100 µT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 µT.

Alkali metal atoms in the vapor phase in the chamber 175 of an optically-pumped magnetometer depolarize upon contact with the internal surfaces 173 of the vapor cell 170 (FIG. 1B). This depolarization limits the coherence lifetime of the spin ensemble. Anti-relaxation coatings can reduce the chances of spin depolarization upon alkali metal vapor contact with the wall, sometimes enabling up to 10,000 bounces before depolarization occurs.

Many conventional coatings employ either a) various paraffins, alkenes or related molecules for non-covalent adhesion or b) octadecyltrichlorosilane (OTS), a hydrocarbon molecule with a silyl head group for covalent binding. Limitations of conventional coatings using paraffin, alkane, or alkene coatings include: a) the bonding type is non-covalent and not uniform and may be difficult to quantitatively reproduce and b) paraffin and related hydrocarbon materials have relatively low melting points and so their use may be restricted to devices operable at low temperatures.

With respect to conventional coatings using OTS, although the bonding is covalent, the anti-relaxation effect is relatively limited. This may be due to the presence of residual electronegative chlorine atoms in the coating after a surface is modified using OTS as an anti-relaxation coating. Surface-bound coatings, such as octadecyltrichlorosilane (OTS), may present residual electronegative chlorine atoms in the coating after binding to an oxide surface. The presence of any electronegative atom, even in an inner position of a hydrocarbon coating, could increase surface polarization compromising anti-relaxation properties of the coating. Accordingly, new coatings and coating materials are disclosed herein to circumvent the expected reduction in spin-decoherence.

OTS (octadecyltrichlorosilane) binds with oxide surfaces, such as aluminum oxide or silicon dioxide, through a covalent reaction of surface-exposed hydroxy groups with the trichlorosilyl group present in an OTS molecule to remove the chlorine moieties and form silicon-oxygen bonds. Ideally, all three chlorine groups present in an OTS molecule would react with three hydroxyl (OH) groups in close proximity to each other on the surface. It is believed, although reliance on this belief is not necessary to the invention, that OTS may not react completely with the oxide surface due to unavailability of three exposed hydroxyl groups on the surface within proximal distance of each other for the formation of three silicon-oxygen bonds.

Figure 3:
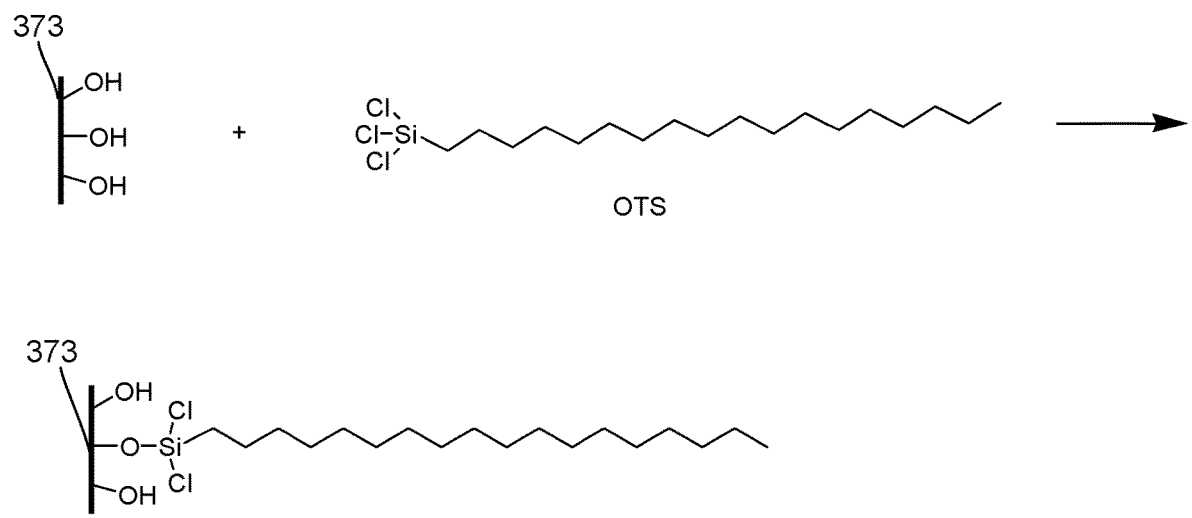
FIG. 3 illustrates a reaction of octadecyltrichlorosilane with an oxide-containing surface.

FIG. 3 illustrates a reaction of OTS with an oxide-containing surface 373 (for example, a surface containing an oxide such as aluminum oxide or silicon dioxide), such as the interior surfaces 173 of the vapor cell 170 of FIG. 1B, with exposed hydroxyl groups. For example, the vapor cell 170 may be made of glass, quartz, or sapphire and present a surface containing an oxide such as aluminum oxide or silicon dioxide. In the example presented in FIG. 3, when reacted, OTS attaches to one of the hydroxyl groups of the surface 373, but the remaining hydroxyl groups on the surface 373 are site-isolated from the OTS molecule because those hydroxyl groups are not close enough to form a bond with the silicon atom of OTS. As exemplified in FIG. 3, when the reaction is completed, one or two chlorine groups of OTS may remain attached to silicon after the surface 373 is modified with OTS due to the lack of proximate hydroxyl groups on the oxide-containing surface. It is believed, although reliance on this belief is not necessary to the invention, that these remaining unbound electronegative chlorine atoms present in the coatings may compromise the anti-relaxation properties of the modified surface. In such instances, the surface, modified by OTS, contains unbound electronegative polarizable chlorine atoms which may compromise the anti-relaxation properties of the surface.

To address the deficiency arising from unbound chlorine atoms in the OTS coatings, a formulation for anti-relaxation coatings can include one or more of the following mono- or dichlorosilane compounds:

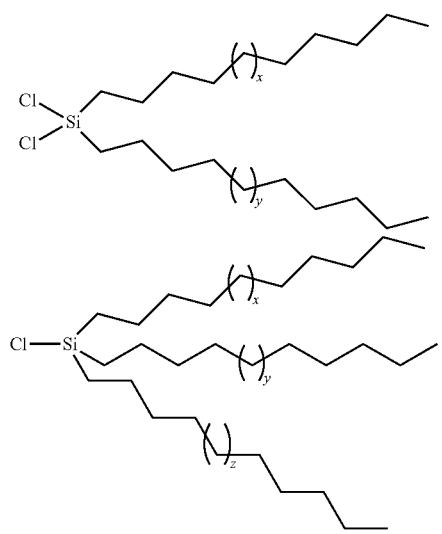

where x, y, and z, are each independently an integer in the range of 0 to 40. In at least some embodiments, x, y, and z are each independently in the range of 5 to 25. In at least some embodiments, x and y are equal. In at least some embodiments, x and z are equal. In at least some embodiments, x, y, and z are equal.

Figure 4:
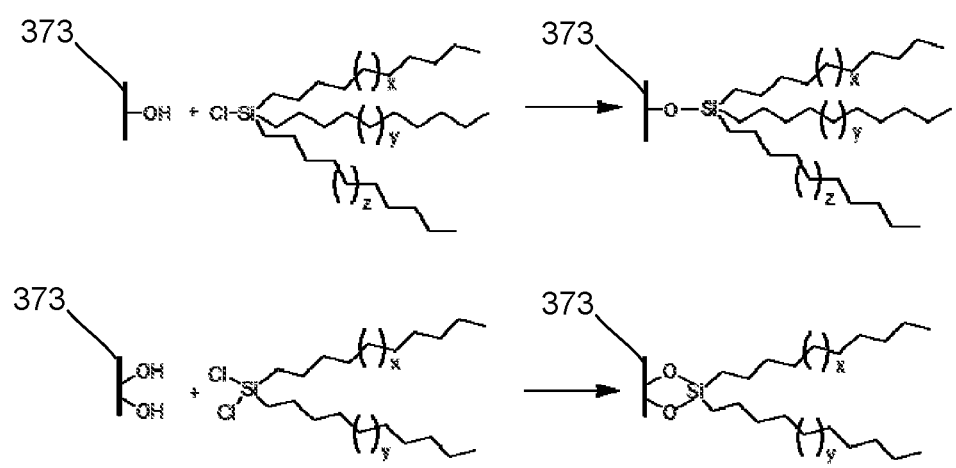
FIG. 4 illustrates reactions of a monochlorosilane and dichlorosilane, respectively, with an oxide-containing surface, according to the invention.

These mono- and dichlorosilane molecules only have one or two chlorine atoms available for oxide surface binding and include one or two additional hydrocarbon chains as compared to OTS. FIG. 4 illustrates the reactions of a monochlorosilane compound and a dichlorosilane compound, respectively, with an oxide-containing surface 373 having one or more hydroxyl groups (for example, a surface containing aluminum oxide or silicon dioxide).

In at least some embodiments, one or more of the monochlorosilane or dichlorosilane compounds identified above are combined with a solvent. Examples of suitable solvents include, but are not limited to, chloroform, hexanes, toluene, or the like or any combination thereof. In at least some embodiments, the monochlorosilane or dichlorosilane compound(s) have a concentration of no more than 1%, 0.5%, or 0.1% in the solvent. The solution is applied to the surface 373 in any suitable manner including, but not limited to, dip coating, spray coating, roll coating, brush coating, or the like. The monochlorosilane or dichlorosilane compound(s) are allowed to react with the surface. In at least some embodiments, the surface may be heated to facilitate reaction. After reaction, the surface may be washed to remove the solvent and any unreacted mono- or dichlorosilane.

These monochlorosilane and dichlorosilane coatings can increase surface anti-relaxation property substantially relative to OTS. The monochlorosilane and dichlorosilane molecules contain only one or two chlorine groups to react with an oxide-containing surface 373, reducing or eliminating the presence of any residual unbound electronegative chlorine groups on the surface and in the coating. Thus, upon covalent binding of the monochlorosilane and dichlorosilane molecules onto the oxide-containing surface 373, the modified surface may have few or no unbound polarizable electronegative groups or atoms.

The monochlorosilane and dichlorosilane compounds contain two or three hydrocarbon chains attached to the silyl group. In at least some embodiments, these compounds can provide for a substantially denser hydrocarbon coatings on an oxide-containing surface 373 than OTS. The attachment of the monochlorosilane and dichlorosilane molecules involves stable covalent bond formation which may increase durability or performance (or both) for the resulting coatings. In at least some embodiments, the selection of specific monochlorosilane and dichlorosilane compounds can provide flexibility in hydrocarbon length design allowing, for example, the availability of up to three different carbon chain lengths per silicon atom.

Examples of magnetic field measurement systems in which the embodiments presented above can be incorporated, and which present features that can be incorporated in the embodiments presented herein, are described in U.S. patent application Ser. Nos. 16/213,980; 16/405,382; 16/418,478; 16/418,500; 16/428,871; 16/456,975; 16/457,655; 16/573,394; and 16/573,524, and U.S. Provisional Patent Applications Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; and 62/926,043, all of which are incorporated herein by reference.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A magnetometer, comprising:
   a vapor cell comprising at least one wall, a chamber defined by the at least one wall, and alkali metal atoms disposed in the chamber to produce an alkali metal vapor in the chamber, wherein the at least one wall comprises an oxide-containing interior surface; and
   an anti-relaxation coating disposed on the oxide-containing interior surface of the at least one wall of the vapor cell, wherein the anti-relaxation coating is a reaction product of the oxide-containing interior surface of the at least one wall with at least one mono- or dichlorosilane compound selected from:

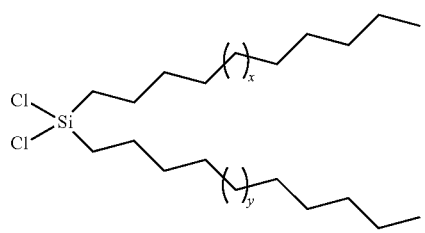

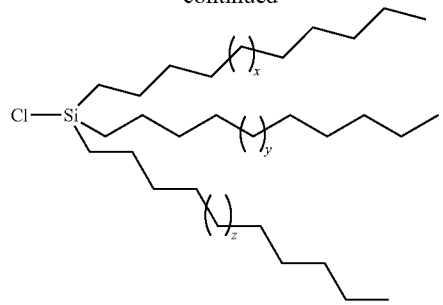

wherein x, y, and z, when present, are each independently an integer in a range of 0 to 40.

2. The magnetometer of claim 1, wherein the at least one mono- or dichlorosilane compound comprises

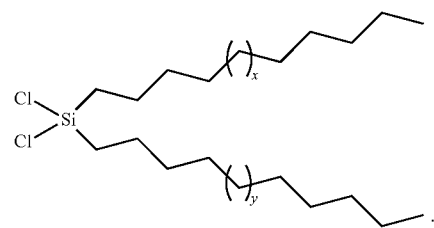

3. The magnetometer of claim 1, wherein the at least one mono- or dichlorosilane compound comprises

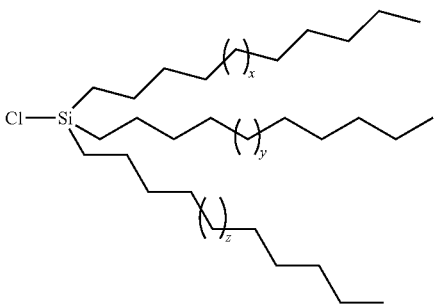

4. The magnetometer of claim 1, wherein x, y, and z, when present, are each independently an integer in a range of 5 to 25.

5. The magnetometer of claim 1, wherein x, y, and z, when present, are equal.

6. The magnetometer of claim 1, wherein the oxide-containing interior surface comprises silicon dioxide.

7. The magnetometer of claim 1, wherein the oxide-containing interior surface comprises aluminum oxide.

8. The magnetometer of claim 1, wherein the vapor cell comprises quartz.

9. The magnetometer of claim 1, wherein the vapor cell comprises sapphire.

10. The magnetometer of claim 1, wherein the vapor cell comprises glass.

11. A magnetic field measurement system, comprising:
    at least one magnetometer of claim 1;
    at least one light source configured for directing light to the at least one magnetometer; and
    at least one detector configured to receive light that passes through the at least one magnetometer.

12. The magnetic field measurement system of claim 11, further comprising at least one magnetic field generator configured to produce a magnetic field at the vapor cell of the at least one magnetometer.

13. The magnetic field measurement system of claim 11, further comprising a computing device coupled to the at least one detector.

14. A method of making the magnetometer of claim 1, the method comprising:
contacting the oxide-containing interior surface of the at least one wall of the vapor cell with the at least one mono- or dichlorosilane compound; and
reacting the mono- or diclorosilane compound with the oxide-containing interior surface to form an anti-relaxation coating on the oxide-containing interior surface.

15. The method of claim 14, wherein the at least one mono- or dichlorosilane compound comprises

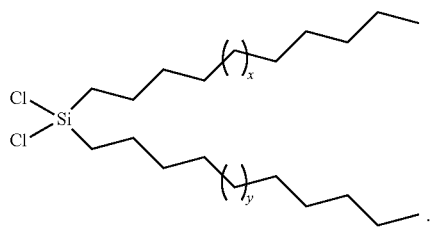

16. The method of claim 14, wherein the at least one mono- or dichlorosilane compound comprises

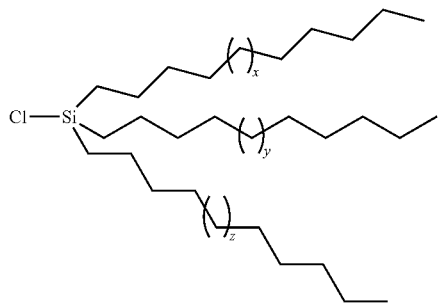

17. The method of claim 14, wherein the oxide-containing interior surface comprises silicon dioxide.

18. The method of claim 14, wherein the oxide-containing interior surface comprises aluminum oxide.

19. The method of claim 14, wherein the vapor cell comprises quartz.

20. The method of claim 14, wherein the vapor cell comprises sapphire.

* * * * *